(12) United States Patent
Pesu et al.

(10) Patent No.: US 6,171,560 B1
(45) Date of Patent: Jan. 9, 2001

(54) SNOW GLOBE AIR FRESHENER AND METHOD OF MANUFACTURE

(75) Inventors: Maxine Truax Pesu, Gahanna; Wendy E. Nitschke, Columbus; Courtland Scott Parker, Westerville, all of OH (US)

(73) Assignee: Bath & Body Works, Inc., Reynoldsburg, OH (US)

( * ) Notice: Under 35 U.S.C. 154(b), the term of this patent shall be extended for 0 days.

(21) Appl. No.: 09/173,279

(22) Filed: Oct. 15, 1998

(51) Int. Cl.[7] .......................................... A61L 9/015
(52) U.S. Cl. .............................. 422/305; 422/4; 422/123; 239/60
(58) Field of Search .................................. 422/4, 5, 120, 422/122, 305, 306, 123, 125; 239/60; 261/DIG. 65, DIG. 17; 392/386

(56) References Cited

U.S. PATENT DOCUMENTS

| | | | |
|---|---|---|---|
| 4,146,566 | * 3/1979 | Gaiser | 422/122 |
| 4,198,375 | * 4/1980 | Rogers | 422/125 |
| 5,187,889 | 2/1993 | Kraselsky et al. . | |
| 5,406,728 | 4/1995 | Willitts, Jr. . | |
| 5,603,176 | 2/1997 | Eddins et al. . | |
| 5,679,334 | 10/1997 | Semoff et al. . | |
| 5,876,678 | * 3/1999 | Harrell et al. | 422/125 |

* cited by examiner

Primary Examiner—Jill Warden
(74) Attorney, Agent, or Firm—Colucci & Umans

(57) ABSTRACT

An air freshener composed of volatile substances having the appearance of a decorative snow globe. A method of making the air freshener is also disclosed.

11 Claims, 1 Drawing Sheet

SNOW GLOBE AIR FRESHENER AND METHOD OF MANUFACTURE

FIELD AND BACKGROUND OF THE INVENTION

The present invention relates generally to air fresheners and in particular to a new and useful decorative air freshener and method for manufacturing the air freshener.

Display articles containing solid objects in a translucent material are known. Snow globes are commonly sold as souvenirs. These snow globes usually have a scene, or object, contained in a spherical enclosure of clear glass or plastic mounted on a flat-bottomed base. The object is surrounded by water or other non-volatile clear liquid. It is also common to have a plurality of small white "flakes" of material in the enclosure, so that when the globe is shaken, the flakes are mixed in the liquid and give the appearance of snow falling on the scene in the enclosure.

Other types of display articles include U.S. Pat. No. 5,603,176, which discloses a jar containing a gel and an object movably suspended within the gel. The gel is a transparent liquid composed of a nontoxic inorganic clay colloidal dispersion in water. In one embodiment disclosed, the jar simulates a fishbowl, with a plastic fish suspended in the gel. A second embodiment includes a gravel base in the bottom of the jar with the gel. While the patent teaches an object suspended in a gel above a gravel base, it is for display purposes only and does not suggest using one or more substances having air freshening properties to support the solid object.

An enclosure with one flat viewing surface in the side is disclosed by U.S. Pat. No. 5,406,728. The enclosure may be made of glass or plastic and contain a figure and a liquid surrounding the figure. The liquid may contain glitter or particles resembling snow flakes. A picture or hologram is applied to the flat surface of the enclosure. Although the display article includes glitter suspended in a liquid, it is also intended solely as a decorative article. The container has only one display face and it is not an air freshener.

U.S. Pat. No. 5,187,889 teaches a globe holding a flowable solid material and solid objects, such as sand and sea shells, which can be shaken to create new decorative scenes. The solid material and solid objects are inserted through a cap opening which is sealed closed to prevent the flowable solid from spilling out of the globe.

Air fresheners formed from volatile liquids which evaporate naturally are also known in the art. For example, an air freshener sold by Bath & Body Works, Inc. has a botanical object supported between layers of an air freshener gel. The air freshener is formed by pouring one layer of gel in liquid form into a container, placing the botanical object partly in the first layer and then pouring a second layer of the gel in liquid form to fill the container and surround the botanical object. The two layers are the same phase and appear to be one continuous translucent layer.

However, the prior art known to the inventor does not teach an air freshener of substantially the same composition in two phases having display articles supported on one phase and surrounded by the second phase.

SUMMARY OF THE INVENTION

It is an object of the present invention to provide an air freshener having decorative properties similar to a snow globe.

It is a further object to provide an air freshener having the appearance of two different substances made from substantially the same components to create a decorative scene with a solid object.

Accordingly, a snow globe air freshener is provided having a first phase of an air freshener composition forming an opaque base gel in a clear container and a second phase of the composition above the first phase forming a translucent or transparent top gel. A solid object may be supported by the base gel in the container and surrounded by the top gel. Small pieces or flakes of a glitter material may be suspended in one or both of the top and base gels as well. Each of the top gel and base gel are volatile with air freshening qualities and evaporate when the container is open.

In a method for making the snow globe air freshener, the base gel is formed from several components mixed together, heated during mixing, poured into a suitable container and cooled to form a cloudy, relatively solid gel. While the base gel is still soft, solid decorative objects can be inserted into the base gel. The clear top gel is composed from a mixture of substantially the same components as the base gel. The top gel is mixed, heated and cooled while the base gel and solid object are cooled further. The top gel is poured into the container down the sides of the container, and upon filling, the entire container is chilled to finish the snow globe. Glitter material may be added to the base gel and/or the top gel.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only drawing of the application is a front exploded elevational view of a snow globe air freshener with lid made according to the invention.

DESCRIPTION OF THE PREFERRED EMBODIMENTS

Figure 1:
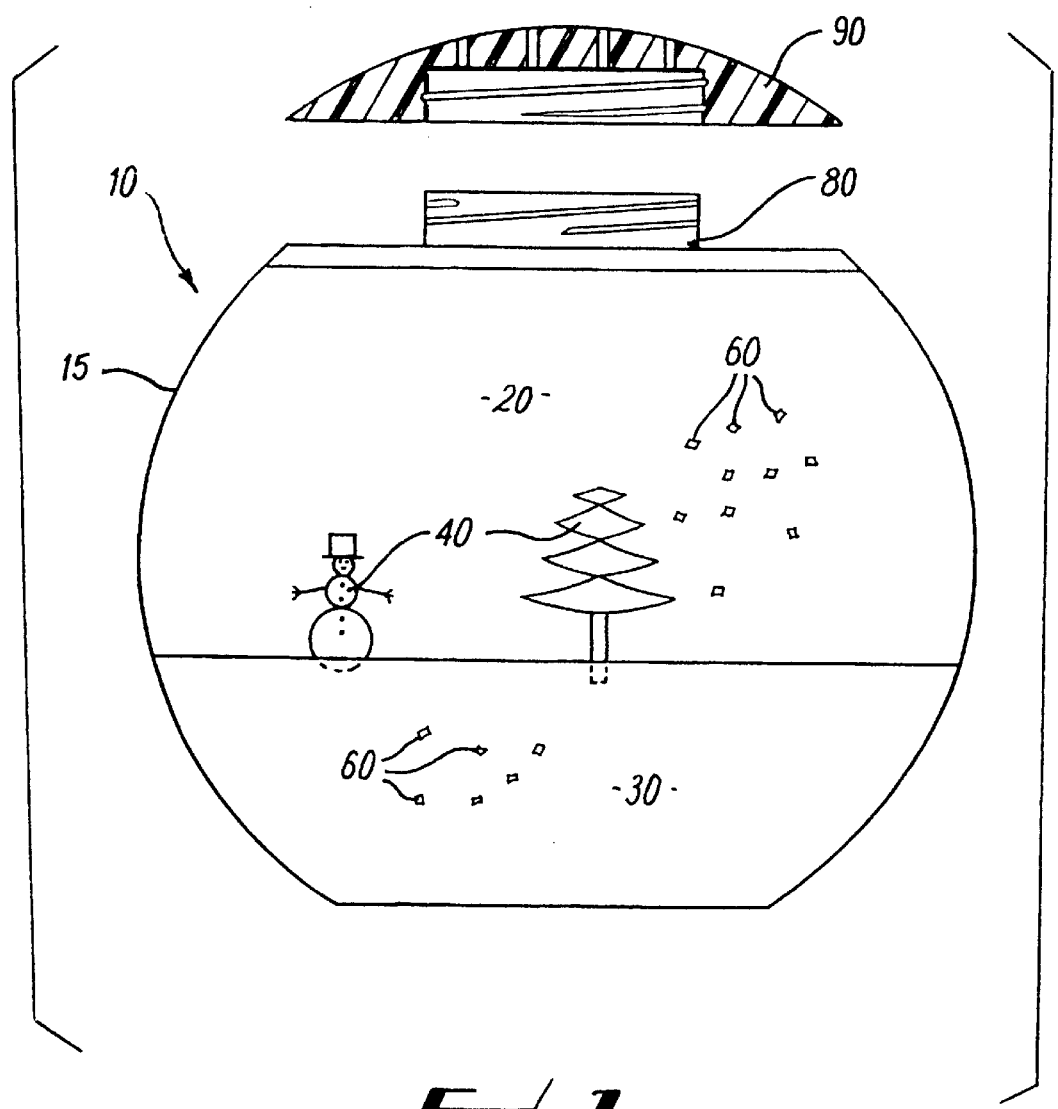

Referring now to the drawing, a snow globe air freshener 10 of the invention has two layers of gel, a base gel 30 and top gel 20 inside a transparent spherical container 15. Decorative objects 40 are located immersed in the top gel and supported on the base gel. As shown in the drawing, a small portion of each object 40 is embedded in the base gel 30. Preferably, between ⅛ inch and ¼ inch of each object 40 is embedded in the base gel 30.

Each of the top gel 20 and base gel 30 can have a glitter material 60 dispersed throughout the gel 20, 30.

The base gel 30 is preferably colored white to resemble a snow covered ground, while the top gel 20 is transparent to permit viewing of the objects 40. The ratio of base gel 30 to top gel 20 in the container 15 is approximately 1:10, but different proportions may be used to create different scenes.

The walls of the container 15 are preferably clear so that the objects 40 may be viewed from any side of the container 15. Thus, the air freshener 10 has the appearance of a decorative snow globe in which, however, the flakes do not move.

The following example provides a method for producing the snow globe air freshener 10 described above.

EXAMPLE

The following table lists the components used to make the base gel 30 and the manufacturer of each component, where applicable:

| Ingredient | Manufacturer | Percent | Range |
|---|---|---|---|
| Deionized Water | | 79.175 | 60–90 |
| Potassium Citrate | Archer Daniels Midland | 0.400 | 0.2–0.6 |
| Bitrex Solution (Super/B-SDA-40B) | Macfarlan Smith Ltd. | 0.050 | 0.0–0.07 |
| Disodium EDTA | Dow Chemical Versene | 0.300 | 0.2–0.4 |
| Gellan Gum | Nutra Sweet | 0.800 | 0.6–1.0 |
| Mica/titanium dioxide | Preperse | 0.200 | 0–0.3 |
| Titanium Dioxide | Whittaker & Clarke | 0.1 | 0–0.2 |
| Octoxynol 13 (Igepal CA-720) | Rhone-Poulenec | 6.000 | 4–8 |
| SD Alcohol 40-2 (190 proof) | Eastman Chemical | 3.000 | 1–5 |
| Dipropylene glycol | Dow Chemical | 5.000 | 2–8 |
| Fragrance Oils | | 5.000 | 2–8 |
| Kathon CGICP | Rohm & Haas | 0.060 | 0.04–0.08 |

The following table lists the components used to make the top gel 20 and the manufacturer of each component, where applicable:

| Ingredient | Manufacturer | Percent | Range |
|---|---|---|---|
| Deionized Water | | 79.347 | 60–90 |
| Potassium Citrate | Archer Daniels Midland | 0.400 | 0.2–0.6 |
| Bitrex Solution (Super/B-SDA-40B) | Macfarlan Smith Ltd. | 0.050 | 0.0–0.07 |
| Disodium EDTA | Dow Chemical Versene | 0.300 | 0.2–0.4 |
| FD&C Blue #1 (.5% H$_2$O/PG) | Warner Jenkinson | 0.003 | 0.0–0.005 |
| Gellan Gum | Nutra Sweet | 0.800 | 0.6–1.0 |
| Polyethylene terephthalate and acrylates copolymer | Meadowbrook Inv. | 0.100 | 0.05–0.2 |
| Octoxynol 13 (Igepal CA-720) | Rhone-Poulenec | 6.000 | 4–8 |
| SD Alcohol 40-2 (190 proof) | Eastman Chemical | 3.000 | 1–5 |
| Dipropylene glycol | Dow Chemical | 5.000 | 2–8 |
| Fragrance Oils | | 5.000 | 2–8 |
| Kathon CGICP | Rohm & Haas | 0.060 | 0.04–0.08 |

Using the above materials, the base gel 20 is prepared first by mixing the deionized water, potassium citrate, bitrex solution and disodium EDTA in a steel beaker surrounded by a hot water bath. The mixing may be done with a marine propeller type mixer. This solution, designated A, is temporarily set aside.

The octoxynol 13, SD Alcohol, dipropylene glycol and fragrance oils are mixed in a glass beaker and stirred with a spatula until clear and homogenous. This mixture is designated solution D.

Next, the gellan gum is dispersed in solution A with stirring while heating the mixture to about 80° C. +/−5°. The mixture is stirred until clear, then cooled to 60° C. with constant stirring. The mica/titanium dioxide and titanium dioxide are then added to the mixture while stirring. Solution D is immediately added to the mixture and stirring is continued until the mixture is clear and homogenous. The temperature of the mixture is maintained at about 60° C. with stirring.

The mixture is then cooled to about 55° C. while stirring, at which point the Kathon CGICP is added. After about one minute, the mixture is poured into the container 15 through the top opening 80 and allowed to cool at room temperature for between 5 and 10 minutes.

After cooling at room temperature, the objects 40 are placed gently into the base gel 30 between about ⅛ inch and ¼ inch deep to hold the objects 40 in place. The base gel 30 and objects 40 are allowed to cool at room temperature for another 10–15 minutes.

While the base gel 30 cools, the top gel 20 is prepared using the materials above as follows.

For the top gel 20, the deionized water, potassium citrate, bitrex solution, disodium EDTA and FD&C Blue #1 are mixed in a steel beaker surrounded by a hot water bath. The mixing may be done with a marine propeller type mixer. This solution, designated A2, is temporarily set aside.

As with the base gel 30, the top gel 20 components octoxynol 13, SD Alcohol, dipropylene glycol and fragrance oils are mixed in a glass beaker and stirred with a spatula until clear and homogenous. This mixture is solution D.

The gellan gum is added to solution A2 with stirring while heating the mixture to about 80° C. +/−5° C. The mixture is stirred until clear, and then it is cooled to about 60° C. while stirring. The polyethylene terephthalate and acrylates copolymer are added to the mixture while stirring, followed immediately by the addition of solution D. The mixture is stirred until it is clear and homogenous while keeping the temperature at about 60° C.

The temperature is then lowered to about 55° C. and the Kathon CGICP is added to the mixture while stirring for about 1 minute.

The top gel 20 mixture is immediately poured down the sides of the container 15 to prevent bubbles from forming in either the top gel 20, the base gel 30 or the interface between them. As soon as the container 15 is filled to an acceptable level with the top gel 20, it is placed in a chilled ice bath at a temperature of between 2–3° C. for 30 minutes. The bath should surround the entire container 15 up to the top opening 80. The low temperature is necessary to keep the polyethylene terephthatlate dispersed throughout the gels 20, 30 and prevent it from settling in the bottom of the container 15.

The container 15 may then be capped and sealed for later use after cooling. The container 15 may be provided with a threaded neck at the top opening 80 for alternately connecting a solid lid (not shown) to seal the container 15 or a lid with perforations 90, to permit the air freshener to evaporate into the atmosphere of a room it is located within.

While specific compositions have been related for use in making the gels 20, 30, it is possible to substitute different compositions having similar properties. For example, the octoxynol 13 may be replaced with another strong surface active agent having good hydrophilic qualities. DMDM Hydantion, such as DANATOGUARD PLUS made by Lonza, may be used in place of Kathon CGICP. Alternatively, a different preservative having similar properties to these two compositions may be used.

Similarly, the potassium citrate and gellan gum may be replaced by a different carrageenan gum system which is clear when mixed and gelled as in the above examples.

Further, the chilling step may be accomplished using a rapid cooling tunnel or a freezer or refrigerator capable of achieving the same temperature and cooling conditions as the ice bath.

While a specific embodiment of the invention has been shown and described in detail to illustrate the application of the principles of the invention, it will be understood that the invention may be embodied otherwise without departing from such principles.

What is claimed is:

1. An air freshener having the appearance of a decorative snow globe, comprising:
   a transparent container having a top opening;
   a volatile opaque colored base gel layer having air freshening qualities filling at least a lower portion of the container;
   a volatile top gel layer which is translucent and having air freshening qualities filling at least an upper portion of the container above the base gel and forming a distinct interface with the opaque base gel layer; and
   at least one solid object immersed in the top gel layer to form a decorative scene with the base gel layer and the top gel layer.

2. An air freshener according to claim 1, wherein the top gel layer and the base gel layer are substantially the same composition in different phases.

3. An air freshener according to claim 2, wherein the container is at least partially spherical.

4. An air freshener according to claim 2, wherein the at least one object is partly embedded in the base gel layer.

5. An air freshener according to claim 4, wherein at least one of the base and top gel layers further comprises a glitter material randomly dispersed and fixed throughout the layer.

6. An air freshener according to claim 2, wherein at least one of the base and top gel layers further comprises a glitter material randomly dispersed throughout the layer.

7. An air freshener according to claim 1, wherein the top gel layer comprises a mixture of deionized water, potassium citrate, disodium EDTA, gellan gum, mica and titanium dioxide, octoxynol 13, SD alcohol, dipropylene glycol and Kathon CGICP.

8. An air freshener according to claim 7, wherein the base gel layer comprises a mixture of deionized water, potassium citrate, bitrex solution, disodium EDTA, gellan gum, mica and titanium dioxide, octoxynol 13, SD alcohol, dipropylene glycol, a fragrance oil and Kathon CGICP.

9. An air freshener according to claim 1, wherein the top gel layer comprises a mixture of a clear gel system, a suitable surface active agent to solublize the fragrance, a preservative, deionized water, disodium EDTA, polyethylene terephthalate and acrylates polymer, SD alcohol and dipropylene glycol.

10. An air freshener according to claim 9, wherein the base gel layer comprises a mixture of a clear gel system, a suitable surface active agent to solublize the fragrance, a preservative, deionized water, disodium EDTA, mica and titanium dioxide, SD alcohol and dipropylene glycol.

11. An air freshener according to claim 1, wherein the base gel layer comprises a mixture of deionized water, potassium citrate, bitrex solution, disodium EDTA, gellan gum, mica and titanium dioxide, octoxynol 13, SD alcohol, dipropylene glycol, a fragrance oil and Kathon CGICP.

* * * * *